(12) United States Patent
Sterpetti

(10) Patent No.: US 11,963,818 B2
(45) Date of Patent: Apr. 23, 2024

(54) METHOD AND SYSTEM FOR THE MEASUREMENT OF HAEMODYNAMIC INDICES

(71) Applicant: UNIVERSITA' DEGLI STUDI DI ROMA "LA SAPIENZA", Rome (IT)

(72) Inventor: Antonio Vittorio Sterpetti, Cappadocia (IT)

(73) Assignee: UNIVERSITA' DEGLI STUDI DI ROMA LA SAPIENZA, Rome (IT)

( * ) Notice: Subject to any disclaimer, the term of this patent is extended or adjusted under 35 U.S.C. 154(b) by 564 days.

(21) Appl. No.: 16/969,341

(22) PCT Filed: Feb. 14, 2019

(86) PCT No.: PCT/IB2019/051196
§ 371 (c)(1),
(2) Date: Aug. 12, 2020

(87) PCT Pub. No.: WO2019/159094
PCT Pub. Date: Aug. 22, 2019

(65) Prior Publication Data
US 2021/0045708 A1    Feb. 18, 2021

(30) Foreign Application Priority Data
Feb. 15, 2018   (IT) .................. 102018000002712

(51) Int. Cl.
*A61B 8/06*       (2006.01)
*A61B 8/00*       (2006.01)
(Continued)

(52) U.S. Cl.
CPC .............. *A61B 8/06* (2013.01); *A61B 8/0891* (2013.01); *A61B 8/12* (2013.01); *A61B 8/469* (2013.01);
(Continued)

(58) Field of Classification Search
None
See application file for complete search history.

(56) References Cited

U.S. PATENT DOCUMENTS

| 2007/0083099 A1* | 4/2007 | Henderson | A61B 8/488 600/407 |
| 2011/0275936 A1* | 11/2011 | Cho | A61B 8/485 600/438 |

(Continued)

*Primary Examiner* — Shahdeep Mohammed
(74) *Attorney, Agent, or Firm* — Mark Malek; Jonathan Staudt; Widerman Malek, PL

(57) ABSTRACT

Method and relative system for the measurement of haemodynamic indices, said method comprising: acquiring an ultrasound image of at least one segment of an arterial vessel; identifying in said image at least one sample volume; obtaining a time series indicating the blood velocity, or velocity signal (9), in said sample volume and in at least one cardiac cycle; calculating, by means of a processor, a first area (4) equal to the area subtended by the velocity signal (9) between the sample (6) relating to the instant of systole start of said at least one cardiac cycle and the sample (7) of systolic peak; calculating, by means of a processor, a second area (5) subtended by the velocity signal (9) between the sample (7) of systolic peak and the sample (8) relating to the instant of end diastole of said at least one cardiac cycle; calculating the relationship between the second area (5) and the first area (4); selecting a time instant of interest in said at least one cardiac cycle; obtaining the spatial distribution of the velocity in said time instant of interest, or instantaneous distribution of the velocity; identifying the maximum value and the minimum value of the instantaneous distribution of the velocity; and calculating the relationship between the maximum value and the minimum value.

10 Claims, 2 Drawing Sheets

(51) Int. Cl.
*A61B 8/08* (2006.01)
*A61B 8/12* (2006.01)
*G16H 50/30* (2018.01)

(52) U.S. Cl.
CPC ............ *A61B 8/488* (2013.01); *A61B 8/5223* (2013.01); *G16H 50/30* (2018.01)

(56) References Cited

U.S. PATENT DOCUMENTS

| | | | | |
|---|---|---|---|---|
| 2014/0350405 | A1* | 11/2014 | Vajinepalli | A61B 8/488 |
| | | | | 600/454 |
| 2016/0029901 | A1* | 2/2016 | Kuri | A61B 5/022 |
| | | | | 600/301 |
| 2019/0142363 | A1* | 5/2019 | Keidar | A61B 8/06 |
| | | | | 600/454 |

* cited by examiner

METHOD AND SYSTEM FOR THE MEASUREMENT OF HAEMODYNAMIC INDICES

RELATED APPLICATIONS

This application is a national phase application of and claims priority under 35 U.S.C. § 371 of PCT Application No. PCT/IB2019/051196 filed on Feb. 14, 2019 and titled METHOD AND SYSTEM FOR THE MEASUREMENT OF HAEMODYNAMIC INDICES. The content of this application is incorporated herein by reference.

TECHNICAL FIELD OF THE INVENTION

The present invention relates to the area of clinical monitoring and of diagnostic systems and, in particular, the systems and methods of vascular investigation by means of Doppler ultrasonography. In this context, the object of the present invention is a method for measuring haemodynamic indices and the relative system implementing this method. These indices can be used for the monitoring of atherosclerotic disease.

For the purpose of the present description, the expression "monitoring of atherosclerotic disease" refers to monitoring of the progression of possible existing atherosclerotic plaques, the identification of new plaques and the follow-up of arterial revascularization operations, whether performed via bypass surgery or whether they are performed via the endovascular route by means of the application of stents.

STATE OF THE ART

Doppler ultrasonography has now for many years been commonly used for measuring haemodynamic parameters such as, for example, the velocity of the blood in the arterial vessels. In fact, thanks to the interaction between the ultrasounds transmitted by means of a special probe and the erythrocytes in movement in the blood flow, it is possible to obtain a measurement of this velocity by making use of the well-known Doppler effect. Due to the latter, the frequency of the ultrasounds reflected by the erythrocytes in movement varies with respect to the frequency of the ultrasounds coming from the probe and impacting on said erythrocytes, in a manner dependent on the velocity of the same erythrocytes. More particularly the velocity of the erythrocytes and, therefore, of the blood flow is given by the following equation:

$$V = \frac{f_D c}{2 f_0 \cos\theta}$$

where $f_D$ is the frequency of the ultrasounds reflected by the erythrocytes, c is the speed of sound in the blood, $f_0$ is the frequency of the ultrasounds impacting on the erythrocytes, that is the ultrasounds transmitted by the probe, and $\theta$ is the angle between the direction of the beam of ultrasounds impacting and the direction of the blood flow.

The velocity of the blood flow can in this way be calculated and measured in time, so as to obtain a time series of velocity values, or velocity signal. The values assumed by this signal in particular instants have for some time been used as indicators for the diagnosis and follow-up of particular pathological states. For example the systolic peak velocity, commonly known in the field with the acronym PSV (peak systolic velocity) and the velocity of end diastole, otherwise known as EDV (end diastolic velocity), are used as diagnostic indicator of carotid stenosis. In general it is known that the trend of the velocity of the blood during the various phases of the cardiac cycle and the spatial distribution of the velocity can vary in the presence of atherosclerotic disease, whether coronary or carotid or of the abdominal arteries. [Rzucidlo E. M., Zwolak R. M., "*Arterial duplex scanning*", in Rutherford R. B., editor: "*Vascular Surgery*", ed. 6, Philadelphia, 2005]. At the state of art, methods providing for the measurement and the processing of the blood velocity are described in U.S. Pat. No. 6,210,168 B1 where a bilinear interpolation is proposed of the maximum value and the minimum value of an instantaneous distribution of the velocity; and in US 20117196237 A1, where it is described the creation of a velocity vector-marker to be displayed in sample volumes of ultrasound images. Once the presence of an atherosclerotic plaque has been determined and its current extent evaluated and, therefore, the current degree of occlusion of the artery concerned, the problem remains of determining what will be the future evolution of the plaque. Prior art methods (US2010/249620 A1) exist for determining the risk of atherothrombosis (i.e. the risk of plaque rupture) based on the measuring of the diameter value of the lumen by means of ultrasound imaging and on comparing the blood shear stress to a critical threshold blood shear stress, the critical threshold blood shear stress being calculated based on the a reference blood viscosity value, and/or the blood flow velocity value and the diameter value of said lumen at a location corresponding to a location on said plaque.

In fact, even if in the current state the plaque can have such an extension as not to need an operation of revascularization, it is possible that this plaque progresses, in time, reducing the lumen to a clinically significant percentage, that is such as to justify an operation. Also in the case wherein no plaque is currently visible and since it cannot be ruled out that it develops in the future, it could be found to be fundamental to evaluate the risk with appropriate prognostic indices.

As mentioned above, Doppler ultrasonography is used not only for diagnostic purposes but also as an instrument for the follow-up of arterial revascularization operations both by the endovascular route (e.g. operations which foresee the insertion of stents) and surgically (e.g. bypass operations). In these cases it is of vital importance to identify in time the risk that these operations fail due to new occlusions. The success of revascularization operations is, in fact, linked not only to the characteristics of the obstructed section operated on but also the characteristics of the haemodynamic downstream of said section. As will be explained in greater detail here below, the outcome of the revascularization is closely dependent on the peripheral resistances downstream of the section which has been operated on.

SUMMARY OF THE INVENTION

The object of the present invention is, therefore, that of providing a method and relative system allowing measurement of particular haemodynamic indices to be used for the forecast of the evolution of a possible existing atherosclerotic plaque or for the forecast of the development of a plaque in arterial sections currently not yet affected by any obstruction.

This object is achieved by the method that is the subject of the present invention, said method comprising the following steps:

acquiring an ultrasound image of at least one segment of an arterial vessel;

identifying in said image at least one sample volume;

obtaining a time series indicating the blood velocity, or velocity signal, in said sample volume and in at least one cardiac cycle;

selecting a time instant of interest in said at least one cardiac cycle;

obtaining the spatial distribution of the velocity in said time instant of interest, or instantaneous distribution of the velocity;

identifying the maximum value and the minimum value of the instantaneous distribution of the velocity; and calculating the relationship between the maximum value and the minimum value.

The relationship between the maximum value and the minimum value is referred to, for the purpose of the present description, as turbulence index (TI) and can be expressed by the following formula:

$$TI = \frac{V_{Max}(t_{peak})}{V_{Min}(t_{peak})}$$

where $t_{peak}$ is, preferably, but not exclusively, the systolic peak instant. Following experimental studies in vitro and in vivo on animals, it has been seen that the growth factors, such as the growth factor derived from the platelets or PDFG (platelet-derived growth factor), is the basic growth factor of the fibroblasts or BFGF (basic fibroblast growth factor), notoriously responsible for the formation of myointimal hyperplasia first and atherosclerosis later, are produced in high quantities in the zones subjected to high shear stress. [Sterpetti A. V., Cucina A., Morena A. R., Di Donna S., Santoro D'Angelo L., Cardillo B., Cavallaro A., Stipa S. "*Shear stress increases the release of interleukin-1 and interleukin-66 by aortic endothelial cells*", Surgery, 1993 November, 114(5): 911-914], [Sterpetti A. V., Cucina A., Fragale A., Lepidi S., Cavallaro A., Santoro D'Angelo L. "*Shear stress influences the release of platelet derived growth factor and basic fibroblast growth factor by arterial smooth muscle cells*", Eur J Vasc Surg, 1994, 8: 138-142]. The cells more prone to proliferation are, instead, those subjected to low shear stress, since a high shear stress inhibits the proliferation of smooth muscle cells. [Sterpetti A. V., Cucina A., Santoro D'Angelo L., Cardillo B., Cavallaro A., "*Shear stress modulates the proliferation rate, protein synthesis, and mitogenic activity of arterial smooth muscle cells*", Surgery, 1993 June, 113(6): 691-699]. These results produce the hypothesis of how, due to the formation of the atherosclerotic plaque, the contemporary presence of zones with high and low shear stress is necessary. Following further studies in vitro and in vivo on animals it was, finally, possible to highlight how a turbulence index greater than 5 predicts a progression of the atherosclerotic plaque towards a condition of occlusion of the vessels, in particular in the carotids at the level of the bifurcation. A second object of the present invention is, moreover, that of providing a method and relative system which allows the measurement of haemodynamic indices indicative of the peripheral resistances downstream of an arterial reconstruction performed by means of the insertion of a stent by the endovascular route or by means of the creation of a bypass surgically. These indices, by virtue of the fact of being indicative of these resistances, can, then, be used as prognostic indices of the favourable outcome or otherwise of revascularization operations.

This object is achieved by the method that is the subject of the present invention, said method comprising the following steps:

acquiring an ultrasound image of at least one segment of an arterial vessel;

identifying in said image at least one sample volume;

obtaining a time series indicating the blood velocity, or velocity signal, in said sample volume and in at least one cardiac cycle;

calculating, by means of a processor, a first area equal to the area subtended by the velocity signal between the sample relating to the instant of systole start of said at least one cardiac cycle and the systolic peak sample;

calculating, by means of a processor, a second area subtended by the velocity signal between the systolic peak sample and between the sample relating to the instant of end diastole of said at least one cardiac cycle; and calculating the relationship between the second area and the first area;

The sample volume is preferably selected downstream of a region of interest comprising a stent or a section involved in surgical revascularization by means of bypass. For the purpose of the present description, the expression "downstream" is understood to mean that the sample volume is selected in the arterial section comprised between the region of interest and the periphery. The expression "upstream" indicates instead a location between the heart and the region of interest. The relationship between the second area and the first area is colled, for the purpose of the present description, current peripheral resistance index (CPRI) and can be expressed by the following formula:

$$CPRI = \frac{A_{post}}{A_{pre}}$$

where $A_{pre}$ is the area subtended by the velocity signal between the sample relating to the instant of systole start and the instant of systolic peak and $A_{post}$ is the area subtended by the velocity signal between the instant of systolic peak and the instant of end diastole. It is known how the peripheral resistances downstream of the obstructed section, and therefore the velocity of the blood flow, are correlated to the probability of success of revascularization operations [Rzucidlo E. M., Zwolak R. M., "*Arterial duplex scanning*", in Rutherford R. B., editor: "*Vascular Surgery*", ed. 6, Philadelphia, 2005]. Following experimental studies in vitro and in vivo on animals, it has been seen how the peripheral resistances depend on the relationship between the area subtended by the velocity signal after the systolic peak and the area subtended by the velocity signal before the systolic peak. It has been shown, moreover, how a current peripheral resistance index greater than 2 is predictive of the failure of the stent or of the bypass, in particular in the coronary arteries and in the arteries of the lower limbs. Finally, the CPRI can also be used as a prognostic index of the evolution of an atherosclerotic plaque and can be used together with the IT to perform this evaluation. In this case too, a CPRI greater than 2 is indicative of a clinically significant risk that the plaque evolves towards occlusion of the vessel, to the extent of requiring an operation.

The object of the present invention is also a system which allows implementation of the method described above and calculating a single one or both the IT and CPRI indices. This system comprises:
- a duplex ecograph scanner configured for the ultrasound image acquisition of at least one segment of an arterial vessel and for the measurement of the velocity of the blood in said at least one segment and in at least one cardiac cycle;
- at least one input device for allowing an operator to select a sample volume in the arterial segment acquired and/or of a cardiac cycle within a time range of acquisition and/or of a time instant of interest in said at least one cardiac cycle;
- a processor, or computer, configured for the storage, the display and the processing of the images acquired and of the haemodynamic indices measured, said processing comprising the following operations:
  - extracting at least one time series indicating the blood velocity, or velocity signal, from the velocity values measured in said sample volume and in at least one cardiac cycle;
  - calculating, by means of a processor, a first area equal to the area subtended by the velocity signal between the sample relating to the instant of systole start of said at least one cardiac cycle and the systolic peak sample;
  - calculating, by means of a processor, a second area subtended by the velocity signal between the sample relating to the instant of end diastole of said at least one cardiac cycle and the systolic peak sample; and
  - calculating the relationship between the second area and the first area;
- and/or the following steps:
  - selecting a time instant of interest in said at least one cardiac cycle;
  - obtaining the spatial distribution of the velocity in said time instant of interest, or instantaneous distribution of the velocity;
  - identifying the maximum value and the minimum value of the instantaneous distribution of the velocity; and
  - calculating the relationship between the maximum value and the minimum value.

The computer of the system of the present invention can, therefore, be configured for the calculation of only the turbulence index (TI), of only the current peripheral resistances index (CPRI) or for the calculation of both. This computer can, moreover, be configured for the generation of a first alert signal if the CPRI is greater than 2 and/or a second alert signal if the IT is greater than 5.

These and other objects of the present invention will be made clearer by the following detailed description of some preferred embodiments of the present invention, to be understood by way of a non-limiting example of the more general concepts claimed.

BRIEF DESCRIPTION OF THE DRAWINGS

The following description refers to the accompanying drawings, in which:

In FIG. 1 the zones with low shear stress are indicated by means of dotted flow lines, while the zones with high shear stress are indicated by means of unbroken flow lines.

DETAILED DESCRIPTION OF THE INVENTION

Figure 1:
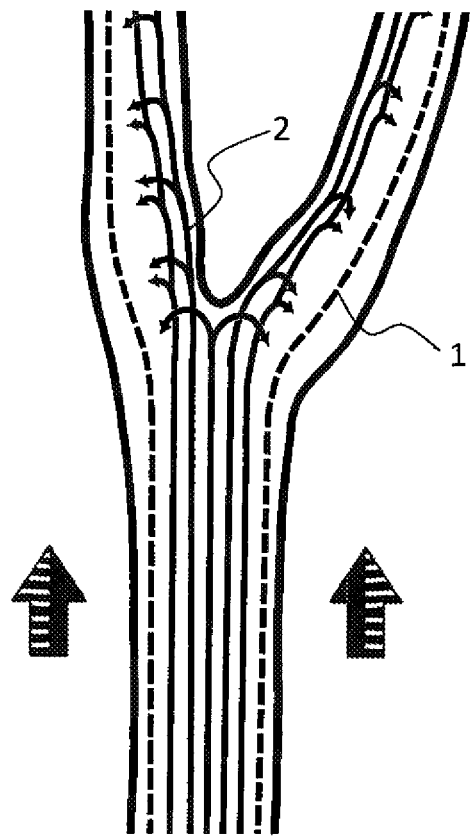
FIG. 1 is a graphic representation of a carotid artery at the level of its bifurcation where the arrows represent the direction of the blood flow.
Figure 2:
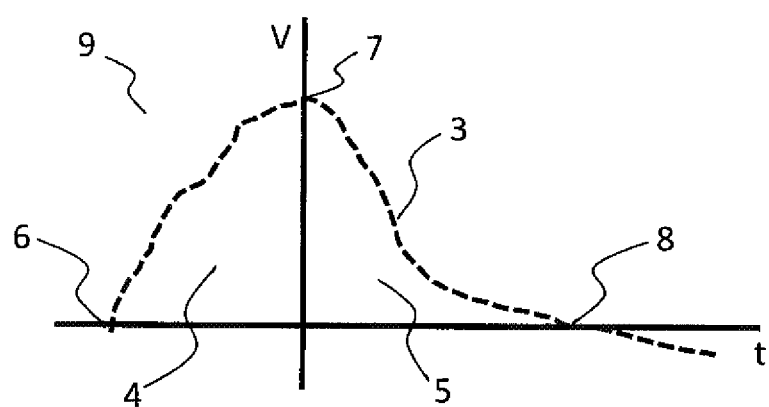
FIG. 2 shows an example of velocity signal in a cardiac cycle.

Referring to FIGS. 1 and 2, a first embodiment of the method of the present invention comprises:
- acquiring an ultrasound image of at least one segment of an arterial vessel;
- identifying in said image at least one sample volume;
- measuring by means of an ultrasound Doppler system the velocity of the blood passing through said sample volume for at least one cardiac cycle;
- selecting a cardiac cycle, if the measuring was performed for more than one cardiac cycle;
- extracting a velocity signal (9) from the velocity values measured, said velocity signal (9) having a length equal to said cardiac cycle and the first sample (6) corresponding to the instant of systole start of said cardiac cycle.
- calculating, by means of a processor, a first area (4) equal to the area subtended by the velocity signal between the sample (6) relating to the instant of systole start of said at least one cardiac cycle and a second sample (7) relating to the instant of systolic peak;
- calculating, by means of a processor, a second area (5) subtended by the velocity signal between the second sample (7) and a third sample (8) relating to the instant of end diastole of said at least one cardiac cycle; and
- calculating the relationship between the second area (5) and the first area (4);

The sample volume can be selected inside a region of interest comprising an atherosclerotic plaque and/or a stent and/or a section involved in surgical revascularization by means of bypass. Alternatively, the sample volume can be selected downstream of this region of interest comprising an atherosclerotic plaque and/or a stent and/or a section involved in surgical revascularization by means of bypass. In the latter case the distance between the sample volume and the region of interest is equal to at least double the length of the plaque and/or of the stent and/or of the section involved in revascularization, said distance being calculated from the end of the plaque or from the mean point of the plaque or of the start of the plaque. For the purpose of the present description, length of the plaque refers to its largest dimension.

Referring to FIGS. 1 and 2, a second embodiment of the method of the present invention comprises:
- acquiring an ultrasound image of at least one segment of an arterial vessel;
- identifying in said image at least one sample volume;
- measuring by means of an ultrasound Doppler system the velocity of the blood passing through said sample volume for at least one cardiac cycle and a second cardiac cycle;
- extracting a first time series from the velocity values measured during the first cardiac cycle, said first series having such a length as to cover the first cardiac cycle and the first sample corresponding to the instant of systole start of the first cardiac cycle;
- extracting a second time series from the velocity values measured, said second series having such a length as to cover the second cardiac cycle and the first sample corresponding to the instant of systole start of the second cardiac cycle; and calculating the velocity signal as series of the mean values between the amplitudes of the second and of the third time series in each time instant.

calculating, by means of a processor, a first area (4) equal to the area subtended by the velocity signal between the sample (6) relating to the instant of systole start of said at least one cardiac cycle and a second sample (7) relating to the instant of systolic peak;

calculating, by means of a processor, a second area (5) subtended by the velocity signal between the second sample (7) and a third sample (8) relating to the instant of end diastole of said at least one cardiac cycle; and calculating the relationship between the second area (5) and the first area (4);

Also in the second embodiment the sample volume can be selected with the same methods explained in detail for the first embodiment.

Referring to FIGS. 1 and 2, a third embodiment of the method of the present invention comprises:
  acquiring an ultrasound image of at least one segment of an arterial vessel;
  identifying in said image at least one sample volume;
  obtaining a time series indicating the blood velocity, or velocity signal, in said sample volume and in at least one cardiac cycle;
  selecting a time instant of interest in said at least one cardiac cycle; said time instant of interest being preferably the systolic peak instant;
  obtaining the spatial distribution of the velocity in said time instant of interest, or instantaneous distribution of the velocity;
  identifying the maximum value and the minimum value of the instantaneous distribution of the velocity; and
  calculating the relationship between the maximum value and the minimum value.

The maximum value will be identified in the zones with low shear stress (1) and the minimum value will be identified in the zones with high shear stress (2).

Referring to FIGS. 1 and 2, a fourth embodiment of the method of the present invention comprises:
  acquiring an ultrasound image of at least one segment of an arterial vessel;
  identifying in said image at least one sample volume;
  measuring by means of an ultrasound Doppler system the velocity of the blood passing through said sample volume for at least one cardiac cycle;
  selecting a cardiac cycle, if the measuring was performed for more than one cardiac cycle;
  extracting a velocity signal (9) from the velocity values measured, said velocity signal (9) having a length equal to said cardiac cycle and the first sample (6) corresponding to the instant of systole start of said cardiac cycle.
  calculating, by means of a processor, a first area (4) equal to the area subtended by the velocity signal between the sample (6) relating to the instant of systole start of said at least one cardiac cycle and a second sample (7) relating to the instant of systolic peak;
  calculating, by means of a processor, a second area (5) subtended by the velocity signal between the second sample (7) and a third sample (8) relating to the instant of end diastole of said at least one cycle;
  calculating the relationship between the second area (5) and the first area (4);
  selecting a time instant of interest in said at least one cardiac cycle; said time instant of interest being preferably the systolic peak instant;
  obtaining the spatial distribution of the velocity in said time instant of interest, or instantaneous distribution of the velocity;
  identifying the maximum value and the minimum value of the instantaneous distribution of the velocity; and
  calculating the relationship between the maximum value and the minimum value.

Referring to FIGS. 1 and 2, a fifth embodiment of the method of the present invention comprises:
  acquiring an ultrasound image of at least one segment of an arterial vessel;
  identifying in said image at least one sample volume;
  measuring by means of an ultrasound Doppler system the velocity of the blood passing through said sample volume for at least one cardiac cycle and a second cardiac cycle;
  extracting a first time series from the velocity values measured during the first cardiac cycle, said first series having such a length as to cover the first cardiac cycle and the first sample corresponding to the instant of systole start of the first cardiac cycle;
  extracting a second time series from the velocity values measured, said second series having such a length as to cover the second cardiac cycle and the first sample corresponding to the instant of systole start of the second cardiac cycle; and
  calculating the velocity signal as series of the mean values between the amplitudes of the second and of the third time series in each time instant.
  calculating, by means of a processor, a first area (4) equal to the area subtended by the velocity signal between the sample (6) relating to the instant of systole start of said at least one cardiac cycle and a second sample (7) relating to the instant of systolic peak;
  calculating, by means of a processor, a second area (5) subtended by the velocity signal between the second sample (7) and a third sample (8) relating to the instant of end diastole of said at least one cardiac cycle;
  calculating the relationship between the second area (5) and the first area (4);
  selecting a time instant of interest in said velocity signal;
    obtaining the spatial distribution of the velocity in said time instant of interest, or instantaneous distribution of the velocity;
    identifying the maximum value and the minimum value of the instantaneous distribution of the velocity; and
    calculating the relationship between the maximum value and the minimum value.

Also in the fourth and in the fifth embodiment the sample volume can be selected with the same methods explained in detail for the first and second embodiments.

The system which allows the implementation of the five embodiments of the method described above comprises:
  a duplex ecograph scanner configured for the ultrasound image acquisition of at least one segment of an arterial vessel and for the measurement of the velocity of the blood in said at least one segment and in at least one cardiac cycle;
  at least one input device for allowing an operator to select a sample volume in the arterial segment acquired and/or of a cardiac cycle within a time range of acquisition and/or of a time interval of interest in said at least one cardiac cycle;
  a processor, or computer, configured for the storage, the display and the processing of the images acquired and of the haemodynamic indices measured.

In a first embodiment of the system of the present invention, this processing comprises the following operations:
- extracting a velocity signal (9) from the velocity values measured, said velocity signal (9) having a length equal to said cardiac cycle and the first sample (6) corresponding to the instant of systole start of said cardiac cycle;
- calculating, by means of a processor, a first area (4) equal to the area subtended by the velocity signal between the sample (6) relating to the instant of systole start of said at least one cardiac cycle and a second sample (7) relating to the instant of systolic peak;
- calculating, by means of a processor, a second area (5) subtended by the velocity signal between the second sample (7) and a third sample (8) relating to the instant of end diastole of said at least one cardiac cycle; and
- calculating the relationship between the second area (5) and the first area (4);

In a second embodiment of the system of the present invention, this processing comprises the following operations:
- extracting a first time series from the velocity values measured during the first cardiac cycle, said first series having such a length as to cover the first cardiac cycle and the first sample corresponding to the instant of systole start of the first cardiac cycle;
- extracting a second time series from the velocity values measured, said second series having such a length as to cover the second cardiac cycle and the first sample corresponding to the instant of systole start of the second cardiac cycle; and
- calculating the velocity signal as series of the mean values between the amplitudes of the second and of the third time series in each time instant.
- calculating, by means of a processor, a first area (4) equal to the area subtended by the velocity signal between the sample (6) relating to the instant of systole start of said at least one cardiac cycle and a second sample (7) relating to the instant of systolic peak;
- calculating, by means of a processor, a second area (5) subtended by the velocity signal between the second sample (7) and a third sample (8) relating to the instant of end diastole of said at least one cardiac cycle; and
- calculating the relationship between the second area (5) and the first area (4);

In a third embodiment of the system of the present invention, this processing comprises the following operations:
- obtaining the spatial distribution of the velocity in a time instant of interest, previously selected by an operator;
- identifying the maximum value and the minimum value of this distribution; and
- calculating the relationship between the maximum value and the minimum value.

In a fourth embodiment of the system of the present invention, this processing comprises the following operations:
- extracting a velocity signal (9) from the velocity values measured, said velocity signal (9) having a length equal to said cardiac cycle and the first sample (6) corresponding to the instant of systole start of said cardiac cycle.
- calculating, by means of a processor, a first area (4) equal to the area subtended by the velocity signal between the sample (6) relating to the instant of systole start of said at least one cardiac cycle and a second sample (7) relating to the instant of systolic peak;
- calculating, by means of a processor, a second area (5) subtended by the velocity signal between the second sample (7) and a third sample (8) relating to the instant of end diastole of said at least one cardiac cycle;
- calculating the relationship between the second area (5) and the first area (4);
- obtaining the spatial distribution of the velocity in a time instant of interest, previously selected by an operator;
- identifying the maximum value and the minimum value of the instantaneous distribution of the velocity; and
- calculating the relationship between the maximum value and the minimum value.

In a fifth embodiment of the system of the present invention, this processing comprises the following operations:
- extracting a first time series from the velocity values measured during the first cardiac cycle, said first series having such a length as to cover the first cardiac cycle and the first sample corresponding to the instant of systole start of the first cardiac cycle;
- extracting a second time series from the velocity values measured, said second series having such a length as to cover the second cardiac cycle and the first sample corresponding to the instant of systole start of the second cardiac cycle; and
- calculating the velocity signal as series of the mean values between the amplitudes of the second and of the third time series in each time instant.
- calculating, by means of a processor, a first area (4) equal to the area subtended by the velocity signal between the sample (6) relating to the instant of systole start of said at least one cardiac cycle and a second sample (7) relating to the instant of systolic peak;
- calculating, by means of a processor, a second area (5) subtended by the velocity signal between the second sample (7) and a third sample (8) relating to the instant of end diastole of said at least one cardiac cycle;
- calculating the relationship between the second area (5) and the first area (4);
- obtaining the spatial distribution of the velocity in a time instant of interest, previously selected by an operator;
- identifying the maximum value and the minimum value of the instantaneous distribution of the velocity; and
- calculating the relationship between the maximum value and the minimum value.

The computer of the system in any one of the five embodiments described above is further configured in order to generate a first alert signal if the relationship between the second area and the first area is greater than 2 and/or a second alert signal if the relationship between the maximum value and the minimum value is greater than 5. The method of the present invention can also be applied in different conditions of the patient and the indices obtained in the different conditions can in turn be combined so as to form new and further indices indicative of pathological states or of the possibility of success of operations of revascularization. More particularly it is possible to perform a measurement of the current peripheral resistances index both in basal conditions and after having performed an injection of papaverine. The relationship between the current peripheral resistances index in basal conditions ($Base_{CPRI}$) and of the peripheral resistances index after injection of papaverine ($Papaverine_{CPRI}$) gives rise to a new prognostic index of the possibility of success or otherwise of the operation of revascularization both in the case of stent and of bypass. This relationship, referred to for the purpose of the present description as predicted peripheral resistances index (PPRI), is, therefore, given by the following equation:

$$PPRI = \frac{CPRI_{Base}}{CPRI_{Papaverine}}$$

A PPRI index lower than 2 presupposes the failure of the arterial reconstruction or revascularization whether performed with stent or by bypass.

The method of the present invention can, therefore, be adapted for the calculation of the PPRI, foreseeing the following steps:
- acquiring an ultrasound image of at least one segment of an arterial vessel;
- identifying in said image at least one region of interest;
- selecting downstream of said region of interest a sample volume;
- obtaining a time series indicating the blood velocity in basal conditions, or base velocity signal, in said sample volume and in at least one cardiac cycle;
- injecting a solution of papaverine:
- obtaining a time series indicating the blood velocity, following the injection of papaverine, or velocity signal after injection of papaverine, in said sample volume and in at least one cardiac cycle;
- identifying in the base velocity signal a sample relative to the instant of systolic peak, or systolic peak sample;
- identifying in the velocity signal after injection of papaverine a sample relative to the instant of systolic peak, or systolic peak sample;
- calculating, by means of a processor, a first area equal to the area subtended by the base velocity between the sample relating to the instant of systole start of said at least one cardiac cycle and the systolic peak sample;
- calculating, by means of a processor, a second area subtended by the base velocity signal between the sample relating to the instant of end diastole of said at least one cardiac cycle and the systolic peak sample; and/or
- calculating a first index as the relationship between the second area and the first area;
- calculating, by means of a processor, a third area equal to the area subtended by the velocity signal after injecting papaverine between the sample relating to the instant of systole start of said at least one cardiac cycle and the systolic peak sample;
- calculating, by means of a processor, a fourth area subtended by the velocity signal after injecting papaverine between the sample relating to the instant of end diastole of said at least one cardiac cycle and the systolic peak sample;
- calculating a second index as the relationship between the fourth area and the third area; and
- calculating the relationship between the first index and the second.

In this context an object of the present invention is also a kit for monitoring of atherosclerotic disease comprising an injectable solution containing papaverine, means for the administration by means of injection of said solution and the system described above.

Finally, here it is specified that the method described above can be implemented at least partially in the form of a program for processor or computer. To this end, this program comprises portions of code which, when performed by said processor, or computer, are apt to implement the method described above. These portions of code can be contained in a medium readable by a processor, or computer, which can be a magnetic medium such as, for example, a hard disk or an optical medium, such as for example a CD-ROM or a DVD or, further, an electronic medium such as ROMs, or flash RAM. The portions of code or, more generally, the information contained in said medium readable by a processor, or computer, can be compressed or encrypted.

The invention claimed is:

1. A method for a measurement of haemodynamic indices, comprising:
   acquiring at least one ultrasound image of at least one segment of an arterial vessel;
   identifying in the at least one ultrasound image at least one sample volume of the at least one segment of the arterial vessel;
   obtaining a time series indicating a blood velocity, or velocity signal, in said at least one sample volume and in at least one cardiac cycle, characterized in that it comprises the following steps:
   calculating, by means of a processor, a first area ($A_{pre}$) equal to an area subtended by the velocity signal between a sample relating to an instant of systole start of said at least one cardiac cycle and a sample relating to an instant of systolic peak;
   calculating, by means of a processor, a second area ($A_{post}$) subtended by the velocity signal between the sample relating to the instant of systolic peak of said at least one cardiac cycle and a sample relating to an instant of diastole end; and
   calculating a current peripheral resistance index (CPRI) relationship between the second area ($A_{post}$) and the first area ($A_{pre}$) according to the following formula:

$$CPRI = \frac{A_{post}}{A_{pre}}$$

wherein the at least one sample volume is at least one of inside a region of interest and downstream the region of interest; and
   wherein the region of interest comprises at least one of a stent and a section involved in a surgical bypass revascularization.

2. The method according to claim 1, wherein a distance between the sample volume that is downstream the region of interest and the region of interest is equal to at least double a length of the stent and/or of the section involved in bypass revascularization, said distance being calculated from at least one of an end of the stent and/or of the section involved in bypass revascularization, a mean point of the stent and/or of the section involved in bypass revascularization, and a start of the stent and/or of the section involved in bypass revascularization.

3. The method according to claim 1, wherein obtaining the velocity signal comprises:
   measuring the blood velocity of blood passing through the at least one sample volume for the at least one cardiac cycle using an ultrasound Doppler system;
   selecting a cardiac cycle, if the measuring was performed for more than one cardiac cycle;
   extracting the velocity signal from the measured blood velocity, said velocity signal having a length equal to said at least one cardiac cycle and the sample corresponding to the instant of systole start of said at least one cardiac cycle.

4. The method according to claim 1, comprising:
  measuring the blood velocity of blood passing through said sample volume for a first cardiac cycle and for a second cardiac cycle using an ultrasound Doppler system;
  extracting a first time series from the blood velocity measured during the first cardiac cycle, said first series having such a length as to cover the first cardiac cycle and a first sample corresponding to the instant of systole start of the first cardiac cycle;
  extracting a second time series from the blood velocity measured during the second cardiac cycle, said second series having such a length as to cover the second cardiac cycle and a second sample corresponding to the instant of systole start of the second cardiac cycle; and
  calculating the velocity signal as series of median values between amplitudes of the first and of the second time series in each time instant.

5. The method according to claim 1, further comprising the following steps:
  selecting a time instant of interest ($t_{peak}$) in said at least one cardiac cycle;
  obtaining a spatial distribution of velocity in said time instant ($t_{peak}$) of interest, or instantaneous distribution of the velocity;
  identifying a maximum value ($V_{MAX}$) and a minimum value ($V_{MIN}$) of the instantaneous distribution of the velocity; and
  calculating a turbulence index (TI) relationship between the maximum value ($V_{MAX}$) and the minimum value ($V_{MIN}$) according to the following formula:

$$TI = \frac{V_{MAX}(t_{peak})}{V_{MIN}(t_{peak})}$$

6. The method according to claim 5, wherein the time instant of interest is the instant of systolic peak of said at least one cardiac cycle.

7. The method according to claim 1, wherein the at least one cardiac cycle comprises at least one basal cardiac cycle and at least one papaverine injection cardiac cycle; wherein the CPRI relationship between the second area ($A_{post}$) and the first area ($A_{pre}$) define a basal current peripheral resistance index ($CPRI_{Base}$) that is associated the at least one basal cardiac cycle; wherein the method further comprises:
  obtaining a time series indicating a blood velocity, or velocity signal, in said at least one sample volume and in the at least one papaverine injection cardiac cycle, characterized in that it comprises the following steps:
  calculating a third area equal to an area subtended by the velocity signal between a sample relating to an instant of systole start of the at least one papaverine injection cardiac cycle and a sample relating to an instant of systolic peak of the at least one papaverine injection cardiac cycle;
  calculating a fourth area equal to an area subtended by the velocity signal between a sample relating to an instant of diastole end of the at least one papaverine injection cardiac cycle and the sample relating to the instant of systolic peak of the at least one papaverine injection cardiac cycle;
  calculating a current peripheral resistance index after injection of papaverine ($CPRI_{Papaverine}$) relationship between the fourth area and the third area according to the following formula:

$$CPRI_{Papaverine} = \frac{Fourth\ Area}{Third\ Area}$$

calculating a predicted peripheral resistance index (PPRI) relationship between the $CPRI_{Base}$ and the $CPRI_{Papaverine}$ according to the following formula:

$$PPRI = \frac{CPRI_{Base}}{CPRI_{Papaverine}}$$

8. A system for a measurement of haemodynamic indices, comprising:
  a duplex ecograph scanner configured to acquire at least one ultrasound image of at least one segment of an arterial vessel and to measure a velocity a velocity of blood in the at least one segment and in at least one cardiac cycle;
  at least one input device for allowing an operator to select at least one sample volume in the at least one ultrasound image acquired of the at least one segment within a time range of acquisition and/or of a time interval of interest in the at least one cardiac cycle;
  characterized in that it further comprises:
    a processor, or computer, configured for storage, display and processing of the at least one ultrasound image acquired and of the velocity of blood measured, said processing comprising the following operations:
      extracting at least one time series indicating the blood velocity, or velocity signal, from the velocity of blood measured in said at least one sample volume and in the at least one cardiac cycle;
      calculating, by means of the processor, a first area ($A_{pre}$) equal to an area subtended by the velocity signal between a sample relating to an instant of systole start of said at least one cardiac cycle and a sample relating to an instant of systolic peak;
      calculating, by means of the processor, a second area ($A_{post}$) subtended by the velocity signal between the sample relating to the instant of systolic peak of said at least one cardiac cycle and the sample relating to an instant of diastole end; and
      calculating a current peripheral resistance index (CPRI) relationship between the second area ($A_{post}$) and the first area ($A_{pre}$) according to the following formula:

$$CPRI = \frac{A_{post}}{A_{pre}}$$

wherein the at least one sample volume is at least one of inside a region of interest and downstream the region of interest; and
  wherein the region of interest comprises at least one of a stent and a section involved in a surgical bypass revascularization.

9. The system according to claim 8 wherein the processing comprises the following steps:
  selecting a time instant of interest ($t_{peak}$) in said at least one cardiac cycle;
  obtaining a spatial distribution of velocity in said time instant of interest ($t_{peak}$), or instantaneous distribution of the velocity in said time instant of interest ($t_{peak}$);

identifying a maximum value ($V_{MAX}$) and a minimum value ($V_{MIN}$) of the spatial distribution of velocity, or the instantaneous distribution of the velocity; and calculating a turbulence index (TI) relationship between the maximum value ($V_{MAX}$) and the minimum value ($V_{MIN}$) according to the following formula:

$$TI = \frac{V_{MAX}(t_{peak})}{V_{MIN}(t_{peak})}$$

10. The system according to claim 9 wherein the computer is further configured in order to generate a first alert signal if the CPRI relationship between the second area ($A_{post}$) and the first area ($A_{pre}$) is greater than 2 and/or to generate a second alert signal if the TI relationship (TI) between the maximum value ($V_{MAX}$) and the minimum value ($V_{MIN}$) is greater than 5.

\* \* \* \* \*